United States Patent [19]
Grundei

[11] Patent Number: 4,895,571
[45] Date of Patent: Jan. 23, 1990

[54] STEM FOR TIBIA PART OF A KNEE JOINT ENDOPROSTHESIS

[75] Inventor: Hans Grundei, Lübeck, Fed. Rep. of Germany

[73] Assignee: S+G Implants GmbH, Lubeck, Fed. Rep. of Germany

[21] Appl. No.: 239,077

[22] Filed: Aug. 31, 1988

[51] Int. Cl.4 ............................................. A61F 2/38
[52] U.S. Cl. .................................................... 623/20
[58] Field of Search ...................... 623/16, 18, 19, 20, 623/21, 22, 23

[56] References Cited

U.S. PATENT DOCUMENTS

| | | | |
|---|---|---|---|
| 2,781,758 | 2/1957 | Chevalier | 623/23 |
| 4,068,324 | 1/1978 | Townley et al. | 623/23 |
| 4,704,686 | 11/1987 | Aldinger | 623/16 |

FOREIGN PATENT DOCUMENTS

| | | | |
|---|---|---|---|
| 0094489 | 11/1983 | European Pat. Off. | 128/924 Z |
| 0118778 | 9/1984 | European Pat. Off. | 128/928 C |
| 913228 | 7/1949 | Fed. Rep. of Germany | 623/16 |
| 2610922 | 2/1982 | Fed. Rep. of Germany | 623/20 |

Primary Examiner—Richard J. Apley
Assistant Examiner—David J. Isabella
Attorney, Agent, or Firm—Balogh, Osann, Kramer, Dvorak Genova & Traub

[57] ABSTRACT

The stem for the tibia part of knee joint endoprostheses has the features that its cross-section is made arcuate at the back and angular medial ridge with the apex pointing in the direction of walking.

1 Claim, 2 Drawing Sheets

STEM FOR TIBIA PART OF A KNEE JOINT ENDOPROSTHESIS

This application is a continuation-in-part of Ser. No. 051,245, filed May 13, 1987, now abandoned, which is a continuation of Ser. No. 783,214, filed Oct. 2, 1985, now abandoned.

BACKGROUND OF THE INVENTION

1. Field of the Invention

The invention relates to a stem for the tibia part of a knee joint endoprosthesis.

2. Description of the Prior Art

In this context, it is known that cross-sections of the two shin bones of a human are shaped as mirror images, with the apices of the triangular cross-sections lying at an angle relative to one another and at an angle to the direction of walking. In order to enable the stems of the tibia parts and knee joint endoprostheses to be inserted in a single position secured against rotation, it was therefore necessary to provide at least one part of the length of the stem with a cross-section in the form of an irregular triangle with rounded corners and outward-curved sides as disclosed in German Patent Specification 2 660 458. This had the consequence however, that different stems for the tibia parts were required for the right knee and left knee, and this greatly increased the stock holding costs.

OBJECTS AND SUMMARY OF THE INVENTION

It is the object of the invention to obtain stems of the same cross-section for the tibia parts for the left and right shin bones, which stems likewise allow virtually only one position, secure against rotation, of the stem or tibia part on insertion into the shin bone.

This object is achieved by a stem for tibia parts of knee joint endoprostheses, wherein the cross-section of the stem has an arcuate contour at the back and a roof-shaped contour at the front with the apex pointing in the direction of walking.

In practice, the stem is thus provided with a cross-section which is obtained in such a way that the two stems for the left and right shin bones are brought into congruence according to German Patent Specification 2 660 458 by pushing them together as mirror images, such that they are congruent with the exception of the two apices of the triangles and that these apices are then cut off.

For implants, this tibia part or the stem can therefore be used for the left knee or right knee. Above all, this substantially simplifies stock holding and reduces its cost. Due to the above mentioned imaginary cutting-off of the apices of the triangles, the corresponding amount of spongy bone also remains in existence in the shin bone on implantation, so that the preparation for the implant also requires less removal of spongy bone.

BRIEF DESCRIPTION OF THE DRAWINGS

The invention will now be described, by way of example, with reference to the accompanying partly diagrammatic drawings, in which.

DETAILED DESCRIPTION OF THE PREFERRED EMBODIMENT

Figure 6:
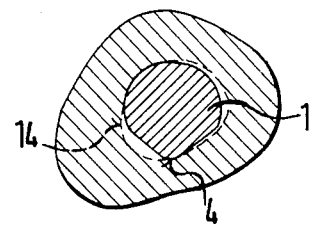
FIG. 6 is a cross-section view of the stem along lines 6—6 of FIG. 5.

A knee endoprosthesis comprises a shaft 10, a plate 12 and a stem 1, the stem 1 being insertable into a cavity 14 in a tibia 16, as shown in FIG. 6.

Figure 1:
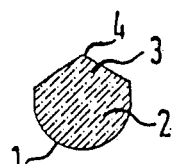
FIG. 1 is a cross-section of the stem of a tibia part according to the invention for a knee joint.
Figure 5:
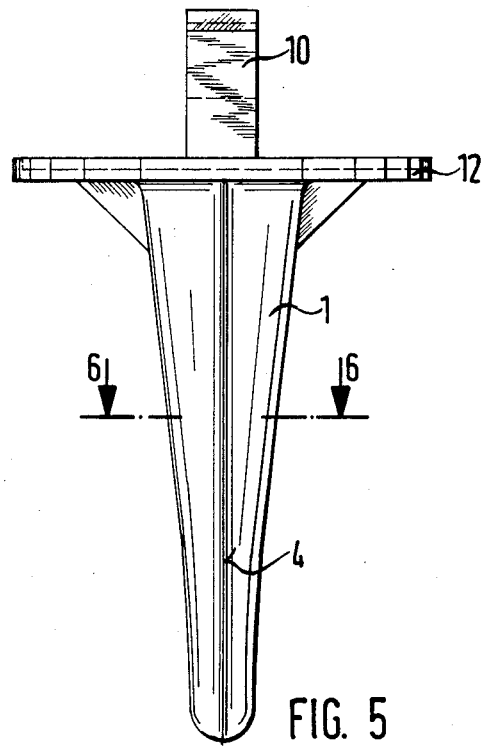
FIG. 5 shows the use of the stem in a knee joint endoprosthesis which includes a shaft and a plate.

According to the invention, the stem 1 for the tibia part of knee joint endoprostheses has a cross-section according to FIG. 1, which is made arcuate, deviating from a circle, in the back part (the lower part in the drawing) and is made triangular roof-shaped in the front part 3 (the upper part of the drawing), with the apex 4 pointing in the direction of walking of the patient.

Figure 2:
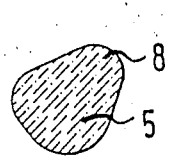
FIGS. 2 and 3 are cross-sections of prior stems for left and right tibia parts respectively.
Figure 3:
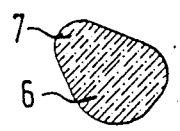
Figure 4:
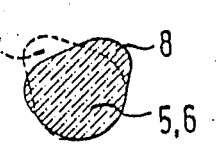
FIG. 4 is a cross-section of the tibia parts of FIGS. 3 and 4 overlayed and brought into congruence.

It may be considered that this cross-sectional profile is built up as follows. If it is imagined that the cross-sections 5 and 6 (FIGS. 2 and 3) of stems for the left and right tibia part or the left and right shin bones are brought into congruence according to FIG. 4 by pushing them together as mirror images, corresponding to German Patent Specification 2 660 458, FIGS. 2 and 3, only the two apices 7 and 8 of the triangles then project beyond the congruent area. These pointed parts 7 and 8 are imagined to be cut off, and the cross-section of the stem according to FIG. 1 is obtained. It is evident that, due to this profile, the stem can assume only one position secure against rotation in both the left and the right shin bone.

What is claimed is:

1. A knee joint endoprosthesis which comprises a elongated shaft for introduction into a prepared medullary cavity, said shaft extending out of one side of a plate, and a stem extending out of the other side of said plate in alignment with a longitudinal axis passing through said shaft, wherein, when the prosthesis is implanted, it is inserted in a space prepared in the medullary bone cavity in the tibia, wherein the cross-sections along the length portions of the stems of both left and right tibias of a patient comprise posterior rounded configurations and planar anterior surfaces terminating in apices pointed in a common direction, the improvement consisting in that the cross-section along the length of said stem is substantially anatomically matched to the cross-sectional shape of the medullary cavity of both left and right tibias, said stem having over its entire length, a posterior surface having a substantially semicircular cross-sectional configuration to match said posterior rounded configuration of said tibias, and an anterior surface having an angular configuration defined by a pair of planar surfaces extending from said posterior surface and angled toward each other to define a continuous medial ridge, said medial ridge being receivable in either of said apices in the right and left tibias.

* * * * *

UNITED STATES PATENT AND TRADEMARK OFFICE
CERTIFICATE OF CORRECTION

PATENT NO. : 4,895,571
DATED : January 23, 1990
INVENTOR(S) : HANS GRUNDEI

It is certified that error appears in the above-identified patent and that said Letters Patent is hereby corrected as shown below:

TITLE PAGE:

after "[22] Filed: August 31, 1988"

insert;

--This application is a Continuation-In-Part of Serial No. 051,245 filed May 13, 1987 (now abandoned), and which was a Continuation of Serial No. 783,214, filed October 2, 1985 (now abandoned).--

Signed and Sealed this

Sixteenth Day of July, 1991

Attest:

HARRY F. MANBECK, JR.

Attesting Officer

Commissioner of Patents and Trademarks